(12) United States Patent
Imai (10) Patent No.: US 7,639,773 B2
(45) Date of Patent: Dec. 29, 2009

(54) X-RAY CT APPARATUS AND METHOD OF GENERATING AN IMAGE

(75) Inventor: Yasuhiro Imai, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/173,748

(22) Filed: Jul. 15, 2008

(65) Prior Publication Data

US 2009/0022263 A1    Jan. 22, 2009

(30) Foreign Application Priority Data

Jul. 18, 2007    (JP) ............... 2007-187234

(51) Int. Cl.
*H05G 1/60* (2006.01)
*H05G 1/64* (2006.01)
(52) U.S. Cl. ............... 378/5; 378/98.11; 378/98.12
(58) Field of Classification Search ............... 378/4, 378/5, 16, 19, 98.9, 98.11, 98.12, 162, 165; 382/130, 132
See application file for complete search history.

(56) References Cited

U.S. PATENT DOCUMENTS

| | | | |
|---|---|---|---|
| 3,974,386 A | 8/1976 | Mistretta et al. | |
| 4,335,427 A | 6/1982 | Hunt et al. | |
| 4,361,901 A | 11/1982 | Daniels et al. | |
| 4,445,226 A | 4/1984 | Brody | |
| 4,482,918 A | 11/1984 | Keyes et al. | |
| 4,559,557 A | 12/1985 | Keyes et al. | |
| 4,611,341 A | 9/1986 | Brody | |
| 4,736,398 A | 4/1988 | Graeff et al. | |
| 4,780,897 A | 10/1988 | McDaniel et al. | |
| 4,945,552 A | 7/1990 | Ueda et al. | |
| 5,396,530 A | 3/1995 | Tsutsui et al. | |
| 6,356,617 B1 | 3/2002 | Besch et al. | |
| 6,922,462 B2 | 7/2005 | Acharya et al. | |
| 6,990,368 B2 | 1/2006 | Simon et al. | |
| 7,221,729 B2 | 5/2007 | Wakai et al. | |
| 2004/0022359 A1 | 2/2004 | Acharya et al. | |
| 2006/0067457 A1* | 3/2006 | Zamyatin et al. ............... 378/4 |

FOREIGN PATENT DOCUMENTS

JP    2004-065975    3/2004

* cited by examiner

*Primary Examiner*—Irakli Kiknadze
(74) *Attorney, Agent, or Firm*—Armstrong Teasdale LLP

(57) ABSTRACT

The present invention provides an X-ray CT apparatus for imaging an MD image having a better S/N. The X-ray CT apparatus for taking an image with one of two materials within a subject to be examined being fractionated, acquiring two sets of data corresponding to said two types of X-ray having different energy by scanning using said two types of X-ray, generating a first image based on the two sets of data with the pixel values made by weighted addition of two types of CT values corresponding to the two types of X-ray, generating a second image based on the two sets of data, wherein the other one of the two types of material being fractionated, and generating an image by weighted subtraction of the first image and the second image.

20 Claims, 6 Drawing Sheets

X-RAY CT APPARATUS AND METHOD OF GENERATING AN IMAGE

CROSS REFERENCE TO RELATED APPLICATIONS

This application claims the benefit of Japanese Patent Application No. 2007-187234 filed Jul. 18, 2007, which is hereby incorporated by reference in its entirety.

BACKGROUND OF THE INVENTION

The subject matter disclosed herein relates to an X-ray CT (computed tomography) apparatus and a method of generating an image, more specifically to an X-ray CT apparatus which makes use of two types of X-ray having different energy to take images with one of two materials within a subject to be examined being fractionated, and a method of generating an image for the use of such X-ray CT apparatus.

When taking images of a specific material fractionated, i.e., MD (material decomposition) images with an X-ray CT apparatus, two types of X-ray which have different energy are used. The scan by means of two types of X-ray each having different energy is also referred to as a dual energy scan.

Because of the energy characteristics of the X-ray absorption coefficient, the data obtained with lower energy X-ray has a value different from the data obtained with higher energy X-ray, and the data ratio will be different according to the material. This characteristic of the X-ray absorption coefficient is made use for taking MD images (for example see JP-A-2004-65975 Japanese Patent Application No. 2004-065975 (paragraphs 0019 to 0023, FIGS. 3 and 4)).

BRIEF DESCRIPTION OF THE INVENTION

For example, when taking MD images with iodine (I) injected as a contrast medium into the subject to be examined, two images are taken with respectively at 80 kV and 140 kV of tube voltage of the X-ray tube to cancel the image of calcium (Ca), which is commonly contained in both images. The cancellation of calcium is performed by weighted subtraction of 140 kV image from 80 kV image. As the weight w, the ratio of CT value of calcium at 80 kV and 140 kV (CT80/CT140) is used. The result of the subtraction may be normalized by $1/(w-1)$.

The CT value ratio of the calcium is given as 1.4 to 1.5; the CT value ratio of the iodine is given as 1.6 to 2.0. The CT value ratio of calcium, for example 1.45, is much closer to 1 than the CT value rate of iodine, for example 1.9, so that the MD image after normalization will have S/N degraded. Otherwise, if performing image processing on the iodine so as to much brighten, distinction of iodine will become difficult from the area having a negative CT value. The similar problem will occur not only with the iodine and calcium in taking MD images also of other material.

The embodiments described herein provide an X-ray CT apparatus which provides MD images having better S/N, and a method of generating an image for such X-ray CT apparatus.

A first aspect provides an X-ray CT apparatus for taking an image with one of two materials within a subject to be examined being fractionated, by using two types of X-ray having different energy, comprising: data acquisition device for acquiring two sets of data corresponding to said two types of X-ray having different energy by scanning using said two types of X-ray; first image generating device for generating a first image based on the two sets of data with the pixel values made by weighted addition of two types of CT values corresponding to the two types of X-ray; second image generating device for generating a second image based on the two sets of data, wherein the other one of the two types of material being fractionated; and third image generating device for generating an image by weighted subtraction of the first image and the second image.

A second aspect provides an X-ray CT apparatus as set forth in the first aspect described above, and is characterized in that the first image generating device generates the first image as an image obtained by the weighted addition of two images, each reconstructed based on the two sets of data.

A third aspect provides an X-ray CT apparatus as set forth in the first aspect described above, and is characterized in that the first image generating device generates the first image by an image reconstruction based on data obtained from the weighted addition of the two sets of data.

A fourth aspect provides an X-ray CT apparatus as set forth in the first aspect described above, and is characterized in that the second image generating device generates the second image as an image obtained by weighted subtraction of two images, each being image reconstructed respectively based on the two sets of data.

A fifth aspect provides an X-ray CT apparatus as set forth in the first aspect described above, and is characterized in that the second image generating device generates the second image by image reconstructing based on data obtained by weighted subtraction of the two sets of data.

A sixth aspect provides an X-ray CT apparatus as set forth in the first aspect described above, and is characterized in that the third image generating device normalizes the pixel value of the weighted subtracted image.

A seventh aspect provides an X-ray CT apparatus as set forth in the first aspect described above, and is characterized in that the two types of X-ray energy are those generated when applying tube voltage of 80 kV and 140 kV respectively to an X-ray tube.

An eighth aspect provides an X-ray CT apparatus as set forth in the first aspect described above, and is characterized in that the two materials are iodine and calcium.

A ninth aspect provides an X-ray CT apparatus as set forth in the first aspect described above, and is characterized in that the two materials are calcium and fat.

A tenth aspect provides a method of generating an image for use in an X-ray CT apparatus for taking an image with one of two materials within a subject to be examined being fractionated, by using two types of X-ray having different energy, the method comprising the steps of: generating a first image based on the two sets of data with the pixel values made by weighted addition of two types of CT values corresponding to the two types of X-ray; generating a second image based on the two sets of data, wherein the other one of the two types of material being fractionated; and generating an image by weighted subtraction of the first image and the second.

An eleventh aspect provides a method of generating an image as set forth in the tenth aspect described above, and is characterized in that the first image is generated as an image obtained by the weighted addition of two images, each reconstructed based on the two sets of data.

A twelfth aspect provides a method of generating an image as set forth in the tenth aspect as have been described above, and is characterized in that the first image is generated by image reconstruction based on data obtained from the weighted addition of the two sets of data.

A thirteenth aspect provides a method of generating an image as set forth in the tenth aspect described above, and is characterized in that the second image is generated as an image obtained by weighted subtraction of two images, each image reconstructed based on the two sets of data respectively.

A fourteenth aspect provides a method of generating an image as set forth in the tenth aspect described above, and is characterized in that the second image is generated by image reconstruction based on data obtained by the weighted subtraction of the two sets of data.

A fifteenth aspect provides a method of generating an image as set forth in the tenth aspect described above, and is characterized in that the pixel value of the weighted subtracted image is normalized.

A sixteenth aspect provides a method of generating an image as set forth in the tenth aspect described above, and is characterized in that the two types of X-ray energy are those generated when applying tube voltage of 80 kV and 140 kV, respectively to an X-ray tube.

A seventeenth aspect provides a method of generating an image as set forth in the tenth aspect described above, and is characterized in that the two types of materials are iodine and calcium.

An eighteenth aspect provides a method of generating an image as set forth in the tenth aspect described above, and is characterized in that the two types of materials are calcium and fat.

In the first aspect, the X-ray CT apparatus for taking an image with one of two materials within a subject to be examined being fractionated, by using two types of X-ray having different energy, comprising: data acquisition device for acquiring two sets of data corresponding to said two types of X-ray having different energy by scanning using said two types of X-ray; first image generating device for generating a first image based on the two sets of data with the pixel values made by weighted addition of two types of CT values corresponding to the two types of X-ray; second image generating device for generating a second image based on the two sets of data, wherein the other one of the two types of material being fractionated; and third image generating device for generating an image by weighted subtraction of the first image and the second image, an X-ray CT apparatus for taking an image having a better S/N may be achieved.

In the tenth aspect, the method of generating an image for use in an X-ray CT apparatus for taking an image with one of two materials within a subject to be examined being fractionated, by using two types of X-ray having different energy, the method comprising the steps of: generating a first image based on the two sets of data with the pixel values made by weighted addition of two types of CT values corresponding to the two types of X-ray; generating a second image based on the two sets of data, wherein the other one of the two types of material being fractionated; and generating an image by weighted subtraction of the first image and the second image, a method of generating an image for use in an X-ray CT apparatus for taking an MD image having a better S/N may be achieved.

In the second and eleventh aspects, the first image as an image obtained by the weighted addition of two images, each reconstructed based on the two sets of data, the image having pixel values as the value obtained from two types of CT values each corresponding to two types of X-ray may be appropriately obtained.

In the third and twelfth aspects, since the first image by an image reconstruction based on data obtained from the weighted addition of the two sets of data, the image having pixel values as the value obtained by weighted addition of two types of CT values each corresponding to two types of X-ray may be appropriately obtained.

In the fourth and thirteenth aspects, since the second image as an image obtained by weighted subtraction of two images, each being image reconstructed respectively based on the two sets of data, an image having the other of two types of materials fractionated may be appropriately obtained.

In the fifth and fourteenth aspects, since the second image by image reconstructing based on data obtained by weighted subtraction of the two sets of data, an image having the other of two types of materials fractionated may be appropriately obtained.

In the sixth and fifteenth aspects, since the pixel value of the weighted subtracted image is normalized, an image having one of two types of materials fractionated may be appropriately obtained.

In the seventh and sixteenth aspects, since the two types of X-ray energy are that energy when applying to an X-ray tube the tube voltage of 80 kV and 140 kV, respectively, an MD image may be appropriately taken.

In the eighth and seventeenth aspects, since the two types of materials are iodine and calcium, an MD image of iodine may be obtained.

In the ninth and eighteenth aspects, since the two types of materials are calcium and fat, an MD image of calcium may be appropriately taken.

DETAILED DESCRIPTION OF THE INVENTION

Embodiments of the invention will be described in greater details herein below with reference to the accompanying drawings. It should be noted here that the present invention is considered not to be limited by the embodiments described herein. Now referring to FIG. 1 there is shown a schematic diagram of an exemplary X-ray CT apparatus.

Figure 1:
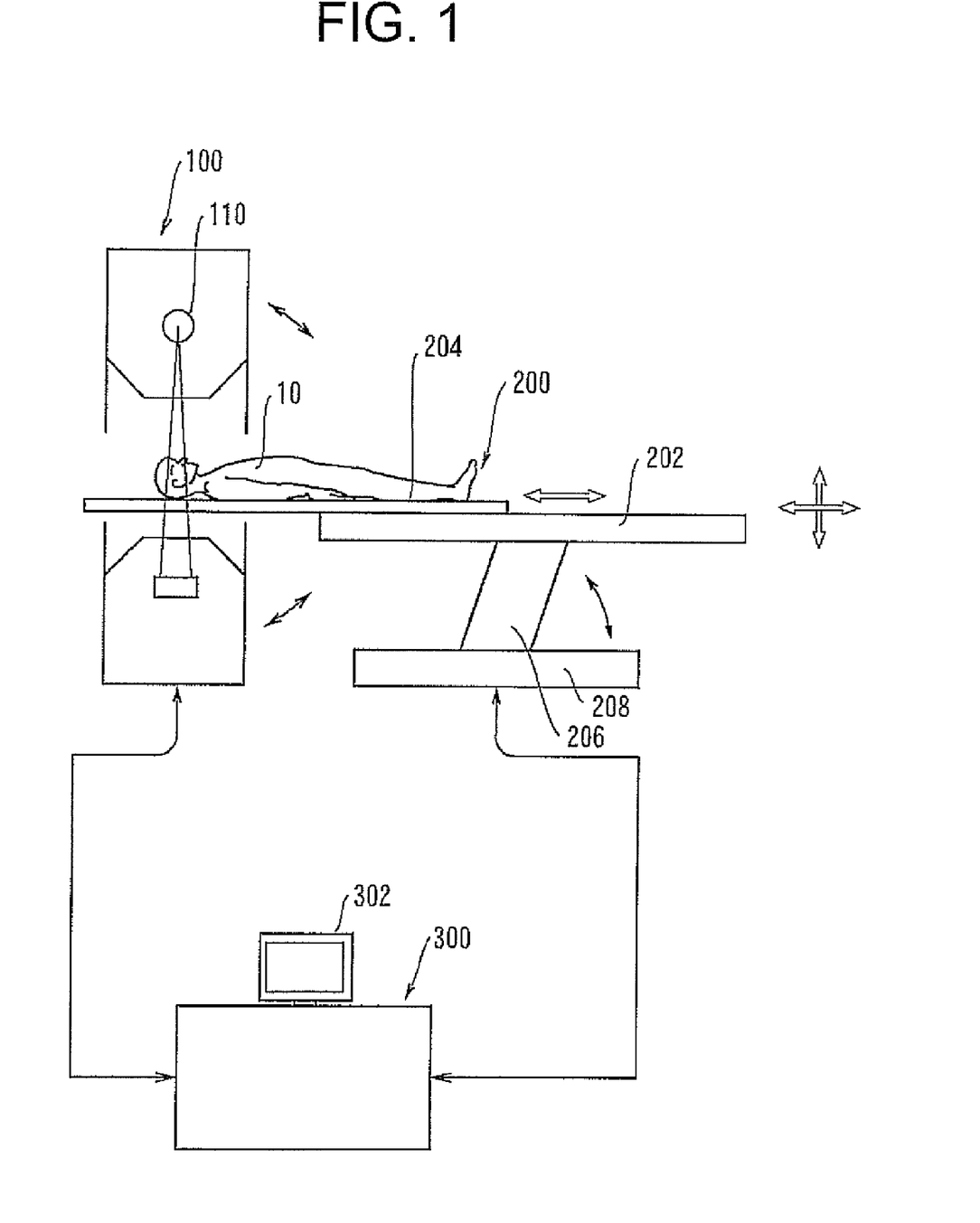
FIG. 1 is a schematic diagram illustrating the arrangement of an exemplary X-ray CT apparatus.

The apparatus has a gantry 100, a table 200, and an operator console 300. The gantry 100 scans by means of an X-ray irradiation and detection device 110 a subject to be examined 10 transported by the table 200 to collect projection data of a plurality of views to input the data to the operator console 300.

The operator console 300 performs the image reconstruction based on the projection data input from the gantry 100 to display thus reconstructed image onto a display 302. The image reconstruction is performed by a dedicated computer in the operator console 300.

The operator console 300 also controls the operation of the gantry 100 and the table 200. The control is performed by a dedicated computer in the operator console 300. Under the control of the operator console 300, the gantry 100 scans under a predetermined scan condition, while the table 200 positions the subject to be examined 10 so as for the predetermined site to be scanned. The positioning is performed by a built-in position adjusting mechanism which adjust the height of the top plate 202 and the horizontal displacement distance of a cradle 204 on the top plate.

An axial scan may be done by performing a scan while the cradle 204 is stopped. A cinescan may be done by sequentially consecutively performing the axial scan for a predetermined period of time.

A helical scan may be performed by performing a plurality of scans in a consecutive manner while moving the cradle 204 continuously. A reciprocal helical scan, i.e., helical shuttle scan may be performed by a reciprocal continuous displacement of the cradle 204 during a helical scan.

The height adjustment of the top plate top plate 202 may be performed by swinging a brace 206 pivotally on the center of attachment point to a base 208. By swinging the brace 206 the top plate top plate 202 will displace in the vertical and horizontal direction. The cradle 204 moves in the horizontal direction on the top plate top plate 202 to cancel out the displacement in the horizontal direction of the top plate top plate 202. Depending on a scanning condition, a scan may be performed by tilting the gantry 100. The tilting of the gantry 100 may be performed by a built-in tilting mechanism.

Figure 2:
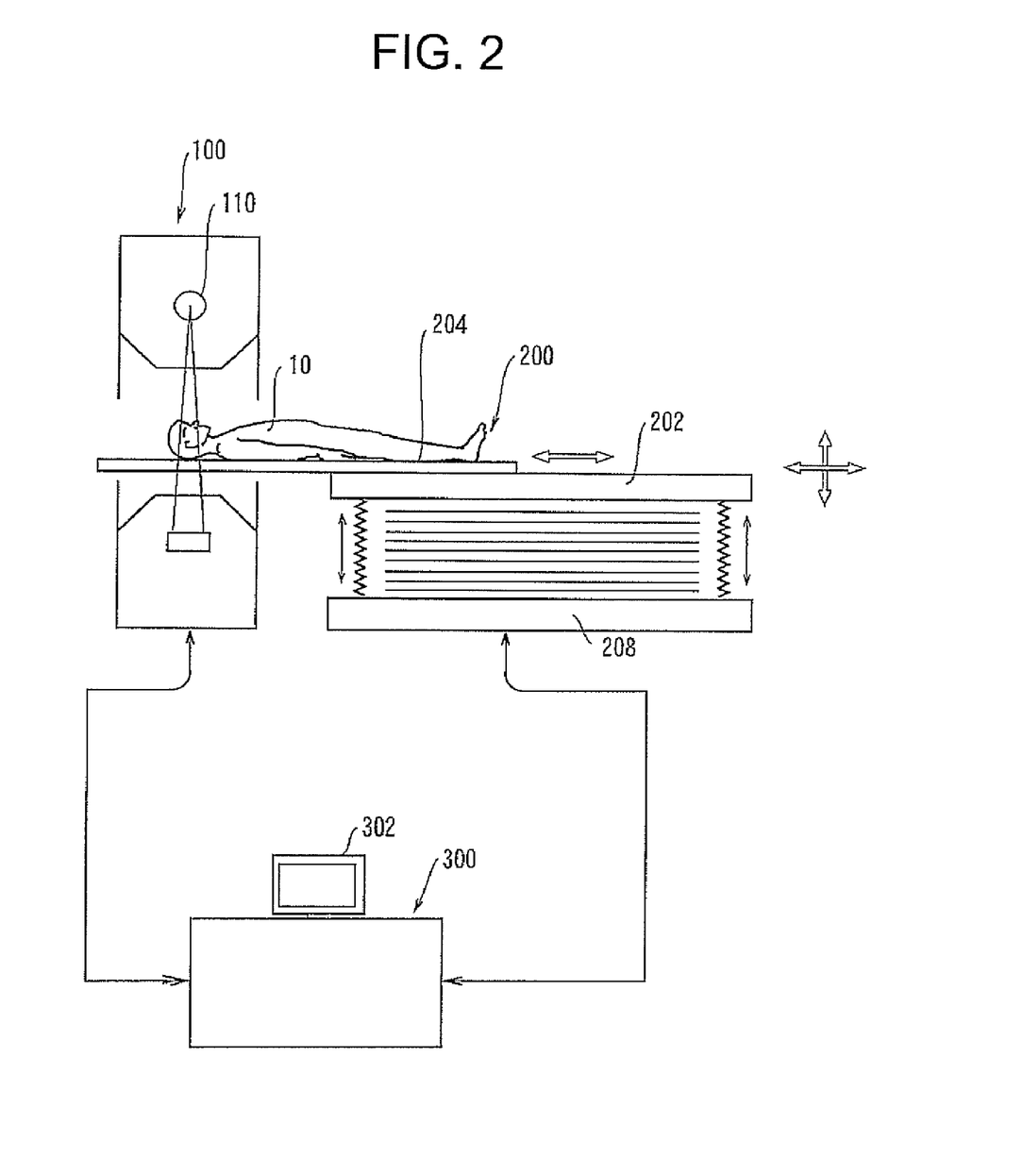
FIG. 2 is a schematic diagram illustrating the arrangement of an exemplary X-ray CT apparatus.

The table 200 may also be a vertical lifting top plate 202 type with respect to the base 208, as shown in FIG. 2. The climb and descent of the top plate 202 may be performed by a built-in elevator mechanism. In such a table 200 the horizontal displacement of the top plate 202 during vertical lifting will not occur.

Figure 3:
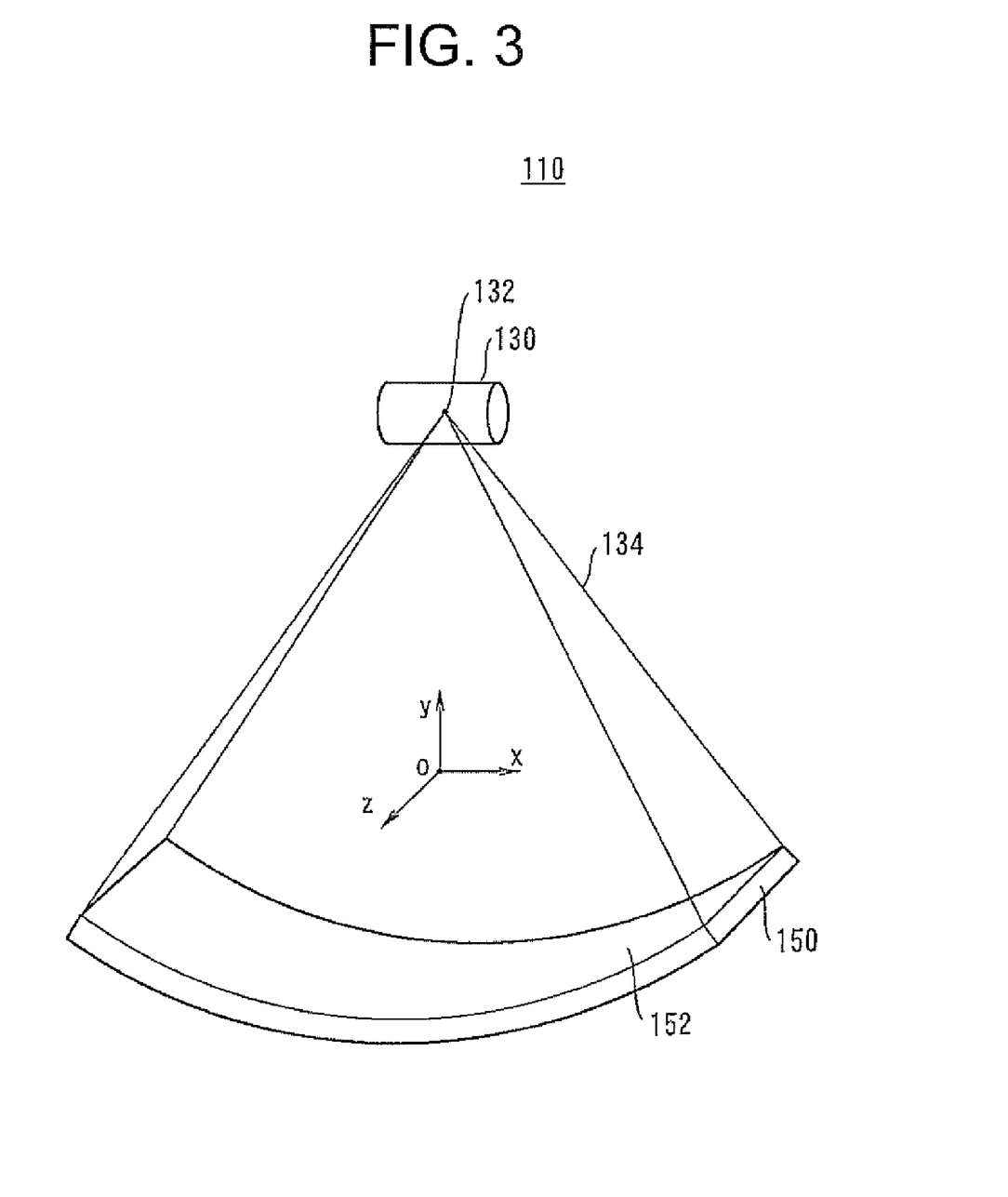
FIG. 3 is a schematic diagram illustrating an X-ray emission and detection device.

Now referring to FIG. 3 there is shown a schematic diagram of the arrangement of an X-ray emission and detection device 110. In the X-ray emission and detection device 110 X-ray 134 emitted from a focus 132 of an X-ray tube 130 is detected by an X-ray detector 150.

The X-ray 134 may be shaped by a collimator not shown in the figure to become a cone beam or a fan beam X-ray. The X-ray detector 150 has an X-ray incidence plane 152, which extends two-dimensionally with respect to the fan out of the X-ray. The X-ray incidence plane 152 is curved so as to be part of a cylinder. The center axis of the cylinder passes through the focus 132.

The X-ray emission and detection device 110 revolves around the center axis that passes the center of imaging i.e., isocenter O. The center axis is placed in parallel to the center axis of the partial cylinder formed by the X-ray detector 150.

Now the direction of revolving center axis is defined as z direction; the direction connecting the isocenter O and the focus 132 is defined as y direction; and the direction perpendicular to both the z direction and y direction is defined as x direction. These x, y, z axes are three axes of rotating coordinate system about z axis as the center axis.

Figure 4:
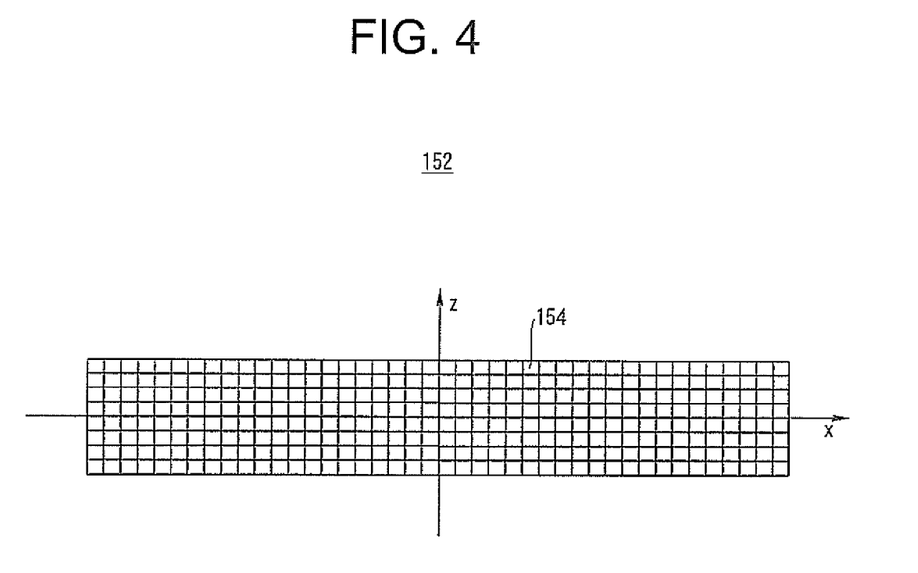
FIG. 4 is a schematic diagram illustrating the X-ray incidence plane of an X-ray detector unit.

Now referring to FIG. 4 there is shown a schematic plan view of the X-ray incidence plane 152 of the X-ray detector 150. In the X-ray incidence plane 152 there are detecting cells 154 placed two-dimensionally in the x direction and z direction. In other words the X-ray incidence plane 152 is a two-dimensional array made of the detecting cells 154. When using fan beam X-ray the X-ray incidence plane 152 may be one-dimensional array of the detecting cells 154.

Each detecting cell 154 constitutes a detection channel of the X-ray detector 150. The X-ray detector 150 will be thereby a multi-channel X-ray detector. The detecting cell 154 may be formed by for example a combination of a scintillator and a photo diode.

Figure 5:
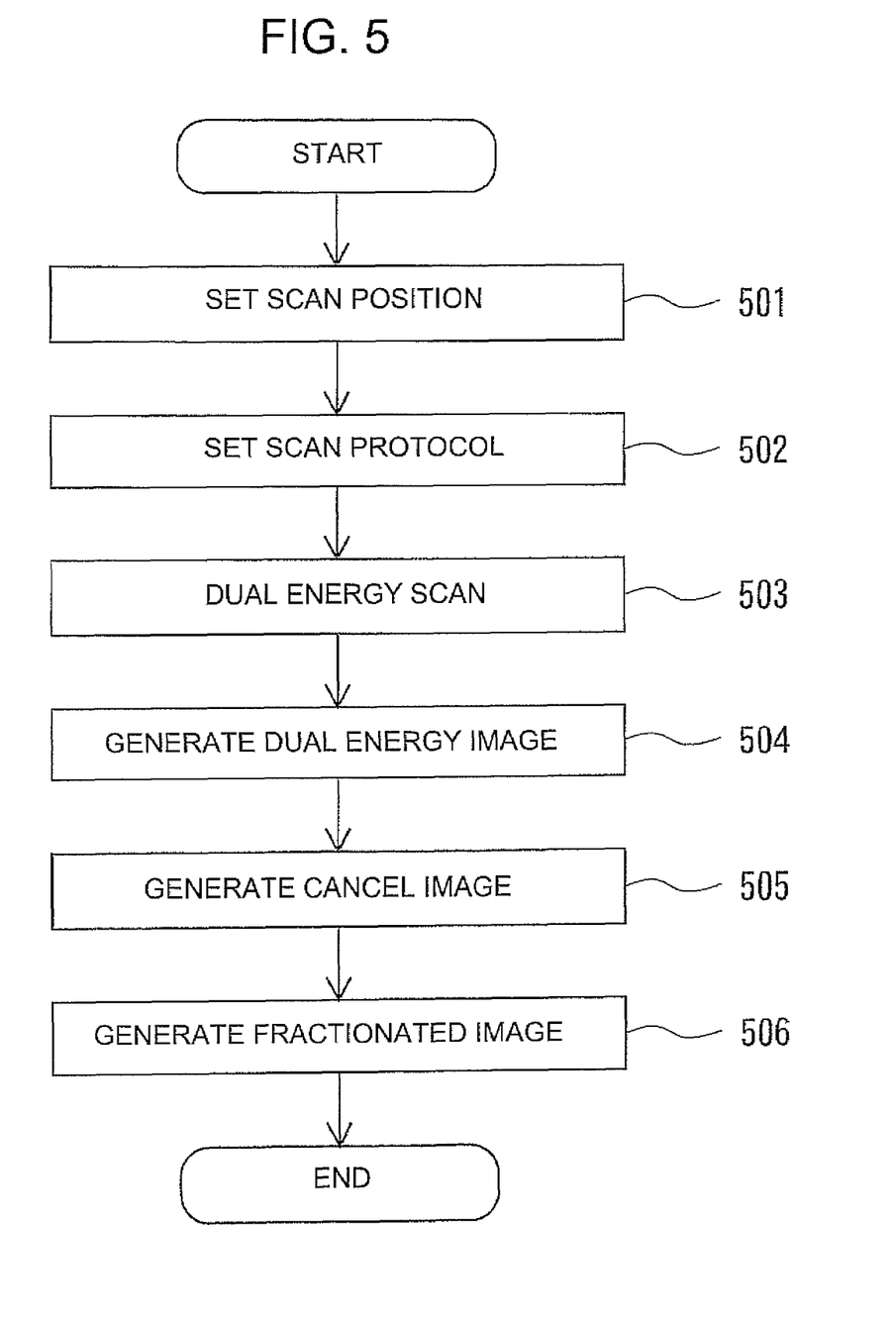
FIG. 5 is a flow diagram illustrating the operation of an exemplary X-ray CT apparatus.

Now referring to FIG. 5 there is shown a flow diagram of the operation of the present apparatus for taking an MD image. Taking an MD image is performed under the control of the operator console 300. As shown by the FIG. 5, in step 501 a scan position is set. The setting of the scan position is done by an operator through the operator console 300.

By doing this, a scan position will be set for example so as to slice perpendicularly the body axis at the largest diameter section of the head. It is needless to say that the scan position is not limited to the head but it may be set at any desired site such as the chest or abdomen.

In step 502 a scan protocol is set. The setting of the scan protocol is performed by the operator through the operator console 300. By this step any required imaging conditions such as the tube voltage and tube current of the X-ray tube, scan speed and sequence duration, image reconstruction condition, MD image generation condition, and the like.

For the tube voltage, for example two voltages, 80 kV and 140 kV may be set. By doing this two types of X-ray energy to be used for the dual energy scan are both set.

In step 503, the dual energy scan is conducted. The dual energy scan is conducted by using a contrast medium. For the contrast medium iodine for example may be used. MD imaging is performed for the purpose of obtaining the fractionated image of iodine.

The dual energy scan is performed by switching alternatively the tube voltage from 80 kV to 140 kV. The switching of the tube voltage is performed every one or more than one views or one scan. One scan consisted of a full scan or a half scan. The full scan is performed by the 360 degrees turn of the X-ray emission and detection device 110. The half scan is performed by 180 degrees plus gamma degrees turn of the X-ray emission and detection device 110. Here gamma indicates the fan angle in the x-y plane of the X-ray 134.

The dual energy scan may also be performed by providing two systems of X-ray irradiation and detection devices 110, with the tube voltage of one system being set to 80 kV and the tube voltage of the other being set to 140 kV, and by irradiate X-ray from both at the same time. In this case the irradiation direction of the X-ray between two X-ray systems are differentiate in 90 degrees for example.

By the dual energy scan, two sets of data correspond to two types of X-ray each having different energy are obtained. One of the two sets of data is the data obtained with the X-ray of maximum energy of 80 keV, and the other is the data obtained with the X-ray of maximum energy of 140 keV.

In step 504, a dual energy image is generated. Here the dual energy image is an image in which the pixel value is the value that two types of CT values corresponding to two types of X-ray having different energy are weighted added. The dual energy image is an example of the first image in accordance with the present invention.

The generation of the dual energy image may be performed by, for example, adding an image obtained by the image reconstruction based on the one of two sets of data with another image obtained by the image reconstruction based on the other of two sets of data.

The CT value of the image reconstructed based on the one of the two sets of data is the CT value under the X-ray of maximum energy 80 keV, and the CT value of the image reconstructed based on the other of the two sets of data is the CT value under the X-ray of maximum energy 140 keV. Because of this the pixel value of the image obtained by adding these two images will be a value of weighted addition of two types of CT values.

The dual energy image may be given by the following equation:

$$M(x,y) = \mathrm{Orig80}(x,y)*a + \mathrm{Orig140}(x,y)*(1.0-a)$$

Here Orig80(x, y) denotes an image based on the X-ray of 80 keV maximum energy, and Orig140(x, y) denotes an image based on the X-ray of 140 keV maximum energy. And 'a' is a coefficient more than 0 and less than 1. Such a dual energy image will have a better S/N in the image.

Alternatively the dual energy image may also be formed by adding two sets of data after the preprocessing and by image reconstructing from the added data, instead of adding images each reconstructed from two sets of data respectively.

In step 505 the cancel image is generated. The cancel image is an image that the shape of unnecessary material is cancelled from the dual energy image. As in this preferred embodiment the unnecessary material is calcium, the fractionated image of calcium is generated as the cancel image. The cancel image is an example of the second image in accordance with the present invention.

The generation of the cancel image is performed by subtracting, from the image obtained by the image reconstruction based on the one of two sets of data, the image obtained by the image reconstruction based on the other of two sets of data, and then by normalizing the addition result.

The cancel image may be given by the following equation:

$$DE(x,y)=(\text{Orig}80(x,y)-\text{Orig}140(x,y)*W)/(W-1.0)$$

Here Orig80(x, y) is the image based on the X-ray of maximum energy 80 keV, Orig140(x, y) is the image based on the X-ray of maximum energy 140 keV. And w may be set to for example 1.9, so as to coincide to the ratio of iodine CT value at 80 keV and at 140 keV. The differential image will be normalized by 1/(w−1.0).

Since w=1.9, the pixel value of iodine will be 0 after the subtraction. Because of this the cancel image will be the fractionated image of the calcium. In contrast, when w=1.45, the pixel value of calcium will be 0 after the subtraction so that the fractionated image of iodine may be obtained. As w=1.9 for obtaining the fractionated image of calcium is much farther from 1 than w=1.45 for obtaining the fractionated image of iodine, the normalized fractionated image of calcium has a better S/N than the fractionated image of iodine.

Alternatively the cancel image may also be obtained by subtracting two sets of data after preprocessing, then by image reconstructing from the subtracted data, instead of subtracting the images each reconstructed from either of two sets of data.

In step 506 a fractionated image is generated. The fractionated image is an example of the third image in accordance with the present invention. The fractionated image is generated by subtracting the cancel image from the dual energy image.

By subtracting the cancel image from the dual energy image, calcium, which is common in both images, will be canceled. With respect to iodine, since iodine in the cancel image is 0, no subtraction is made from the dual energy image. By doing this an image on which iodine resides, i.e., a fractionated image of iodine may be obtained.

The subtraction of cancel image from the dual energy image can be a subtraction made together with an appropriate weighting. By doing this calcium may be canceled appropriately. For the fractionated iodine image, normalization may also be applied thereto. In this manner the contrast may be set appropriately.

Since the fractionated image of iodine is generated by subtracting the fractionated image of calcium having a better S/N from the dual energy image having a better S/N, the final S/N will be better. In other words an MD image of iodine having a better S/N may be obtained. Also since the image processing for whitening iodine is not necessary, the area having a negative CT value will not be whitened as the prior art image.

Although the foregoing description takes an example of MD imaging with respect to iodine, MD imaging is not limited to iodine. A fractionated image of calcium having a better S/N may be obtained by applying the same principle when generating the fractionated image of calcium by making use of difference between the CT value ratio of calcium, 1.4 to 1.5, and the CT value ratio of fat, 0.8 to 0.9. This also applies when performing an MD imaging with respect to the iron (Fe) or Gadolinium (Gd).

Figure 6:
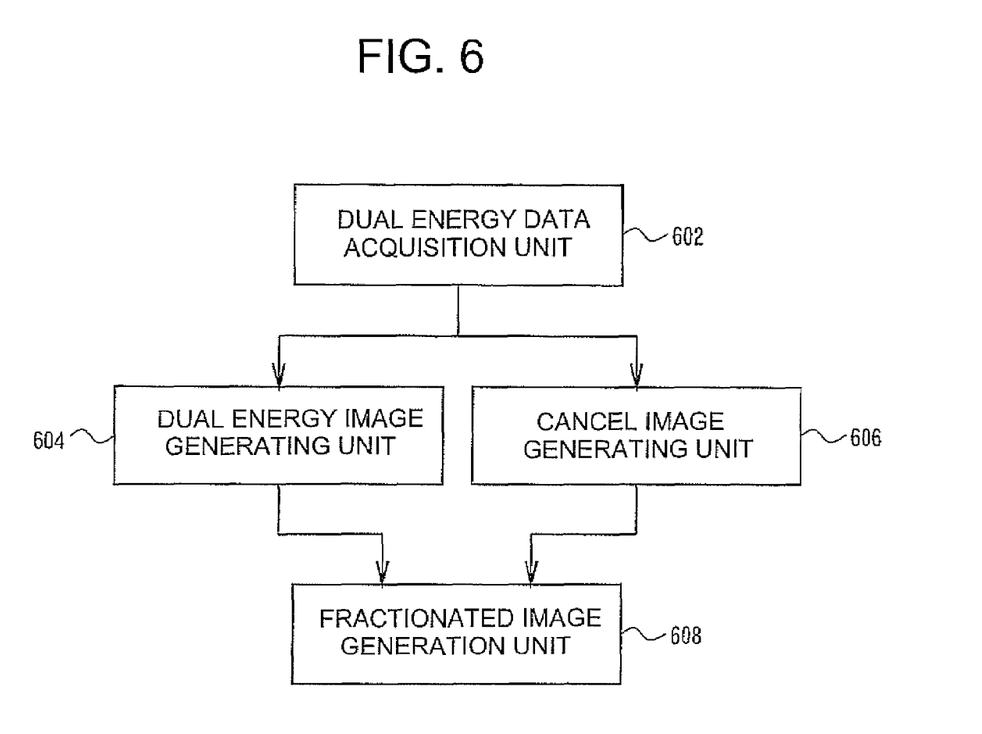
FIG. 6 is a schematic block diagram illustrating the arrangement of an exemplary X-ray CT apparatus.

Now referring to FIG. 6 there is shown a schematic block diagram of the present apparatus in view of MD imaging. As shown in FIG. 6, the apparatus obtains in a dual energy data acquisition unit 602 two sets of data corresponding to two types of X-ray each having different energy. The dual energy data acquisition unit 602 corresponds to the gantry 100 shown in FIG. 1 or FIG. 2. The dual energy data acquisition unit 602 is an example of data acquisition device in accordance with the present invention.

The two sets of data will be input to a dual energy image generating unit 604 and to a cancel image generating unit 606. The dual energy image generating unit 604 generates a dual energy image from these two sets of data, while the cancel image generating unit 606 generates a cancel image from these two sets of data.

The dual energy image generating unit 604 and the cancel image generating unit 606 corresponds to the section concerning to the dual energy image generation and to the section concerning to the cancel image generation unit, both in the operator console 300 shown in FIG. 1 or FIG. 2, respectively. The dual energy image generating unit 604 is an example of the first image generation device in accordance with the present invention. The cancel image generating unit 606 is an example of the second image generation device in accordance with the present invention.

The dual energy image and cancel image will be input to a fractionated image generation unit 608. The fractionated image generation unit 608 generates a fractionated image from the dual energy image and the cancel image. The fractionated image generation unit 608 corresponds to the section concerning to the fractionated image generating unit in the operator console 300 shown in FIG. 1 or FIG. 2. The fractionated image generation unit 608 is an example of the third image generating device in accordance with the present invention.

What is claimed is:

1. An X-ray CT apparatus for taking an image with a first material of two materials within a subject to be examined being fractionated, by using a first set of X-rays at a first energy level and a second set of X-rays at a second energy level, said X-ray CT apparatus comprising:
   a data acquisition device configured to acquire a first set of data corresponding to the first set of X-rays and a second set of data corresponding to the second set of X-rays by scanning using the first set of X-rays and the second set of X-rays;
   a first image generating device configured to generate a first image based on the first set of X-rays and the second set of X-rays, the first image having pixel values made by weighted addition of first CT values corresponding to the first set of X-rays and second CT values corresponding to the second set of X-rays;
   a second image generating device configured to generate a second image based on the first set of data and the second set of data, wherein a second material of the two materials is fractionated in the second image; and
a third image generating device configured to generate the image by weighted subtraction of the first image and the second image.

2. The X-ray CT apparatus according to claim 1, wherein said first image generating device is configured to generate the first image based on the weighted addition of two images, each image of the two images reconstructed based on the first set of data and the second set of data.

3. The X-ray CT apparatus according to claim 1, wherein said first image generating device is configured to generate the first image by an image reconstruction based on data obtained from the weighted addition of the first set of data and the second set of data.

4. The X-ray CT apparatus according to claim 1, wherein said second image generating device is configured to generate the second image based on a weighted subtraction of two images, each image of the two images being image reconstructed based on one of the first set of data and the second set of data.

5. The X-ray CT apparatus according to claim 1, wherein said second image generating device is configured to generate the second image by image reconstructing based on data obtained by weighted subtraction of the first set of data and the second set of data.

6. The X-ray CT apparatus according to claim 5, wherein said third image generating device is configured to normalize pixel values of the weighted subtracted image.

7. The X-ray CT apparatus according to claim 1, wherein the first set of X-rays are these generated when applying a tube voltage of 80 kV to an X-ray tube, and the second set of X-rays are generated when applying a tube voltage of 140 kV to the X-ray tube.

8. The X-ray CT apparatus according to claim 1, wherein the two materials are iodine and calcium.

9. The X-ray CT apparatus according to claim 1, wherein the two materials are calcium and fat.

10. The X-ray CT apparatus according to claim 1, further comprising an operator console configured to receive imaging conditions to be used by said X-ray CT apparatus.

11. A method of generating an image using an X-ray CT apparatus, wherein a first material of two materials within a subject to be examined is fractionated in the image, the method comprising:
acquiring a first set of data using a first set of X-rays at a first energy level and a second set of data using a second set of X-rays at a second energy level;
generating a first image based on the first set of data and the second set of data, the first image having pixel values made by weighted addition of first CT values corresponding to the first set of X-rays and second CT values corresponding to the second set of X-rays;
generating a second image based on the first set of data and the second set of data, wherein a second material of the two materials is fractionated in the second image; and
generating the image by weighted subtraction of the first image and the second image.

12. The method of generating an image according to claim 11, wherein generating a first image comprises the weighted addition of two images, each image of the two images reconstructed based on the first set of data and the second set of data.

13. The method of generating an image according to claim 11, wherein generating a first image comprises an image reconstruction based on data obtained from the weighted addition of the first set of data and the second set of data.

14. The method of generating an image according to claim 11, wherein generating a second image comprises a weighted subtraction of two images, each image of the two images reconstructed based on one of the first set of data and the second set of data.

15. The method of generating an image according to claim 11, wherein generating a second image comprises an image reconstruction based on data obtained by the weighted subtraction of the first set of data and the second set of data.

16. The method of generating an image according to claim 15, further comprising normalizing pixel values of the weighted subtracted image.

17. The method of generating an image according to claim 11, further comprising generating the first set of X-rays by applying a tube voltage of 80 kV to an X-ray tube, and generating the second set of X-rays by applying a tube voltage of 140 kV to the X-ray tube.

18. The method of generating an image according to claim 11, further comprising applying the first set of X-rays and the second set of X-rays to the two materials, wherein the two materials are iodine and calcium.

19. The method of generating an image according to claim 11, further comprising applying the first set of X-rays and the second set of X-rays to the two materials, wherein the two materials are calcium and fat.

20. The method of generating an image according to claim 11, further comprising setting a scan protocol including imaging conditions to be used by the X-ray CT apparatus.

* * * * *